United States Patent
Alarcon Sanchez et al.

(10) Patent No.: US 8,614,231 B2
(45) Date of Patent: Dec. 24, 2013

(54) IMMUNOSUPPRESSOR BASED ON THE BLOCKAGE OF TCR-NCK INTERACTION

(75) Inventors: Balbino Alarcon Sanchez, Madrid (ES); Angel Ramirez Ortiz, Madrid (ES); María del Carmen Fábregas Cleveria, legal representative, Madrid (ES); Maria Luz Ortiz, legal representative, Madrid (ES); Aldo Borroto Revuelta, Madrid (ES); Antonio Morreale de Leon, Madrid (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 223 days.

(21) Appl. No.: 13/001,914

(22) PCT Filed: Jun. 18, 2009

(86) PCT No.: PCT/ES2009/070239
§ 371 (c)(1), (2), (4) Date: Jan. 26, 2012

(87) PCT Pub. No.: WO2010/000900
PCT Pub. Date: Jan. 7, 2010

(65) Prior Publication Data
US 2012/0135041 A1    May 31, 2012

(30) Foreign Application Priority Data

Jun. 30, 2008 (ES) .................................. 200801964

(51) Int. Cl.
*A01N 43/40* (2006.01)
*A61K 31/445* (2006.01)
*C07D 401/00* (2006.01)
*C07D 405/00* (2006.01)
*C07D 409/00* (2006.01)
*C07D 411/00* (2006.01)
*C07D 413/00* (2006.01)
*C07D 417/00* (2006.01)
*C07D 419/00* (2006.01)
*C07D 421/00* (2006.01)

(52) U.S. Cl.
USPC .......................................... 514/320; 546/196

(58) Field of Classification Search
USPC .......................................... 514/320; 546/196
See application file for complete search history.

(56) References Cited

FOREIGN PATENT DOCUMENTS

| WO | 0134591 | 5/2001 |
|---|---|---|
| WO | 02092076 | 11/2002 |
| WO | 03096982 | 11/2003 |

OTHER PUBLICATIONS

International Search Report dated Oct. 5, 2009 in re PCT/ES2009/070239, filed on Jun. 18, 2009.

*Primary Examiner* — Samira Jean-Louis
(74) *Attorney, Agent, or Firm* — Gardner, Groff, Greenwald & Villanueva, P.C.

(57) ABSTRACT

The present invention relates to a compound of structural formula (I) and its derivatives for use as medicinal drugs. They are preferably immunosuppressive agents, with mechanism of action based on the blockage of TCR-Nck interaction.

9 Claims, 8 Drawing Sheets

IMMUNOSUPPRESSOR BASED ON THE BLOCKAGE OF TCR-NCK INTERACTION

IN THE CROSS-REFERENCE TO RELATED APPLICATIONS

This application claims priority to Spanish Application No. P200801964, filed Jun. 30, 2008, which is hereby incorporated by reference in its entirety for all purposes.

The present invention relates to a compound with the structural formula (I)

(I)

and its derivatives for use as medicinal drugs. They are preferably immunosuppressive agents, with mechanism of action based on the blockage of TCR-Nck interaction.

PRIOR ART

T lymphocytes perform a central role in the rejection of allotransplants and are more or less directly involved in the generation of autoimmune diseases. Therefore the mechanism of action of current immunosuppressive pharmaceuticals is based on the inhibition of the activation of T lymphocytes. These immunosuppressors have high toxicity because they do not inhibit lymphocyte pathways in a specific way.

T lymphocytes are activated through the antigen receptor (TCR), which recognises the major histocompatibility complex (MHC) of the transplanted organ as foreign. TCR is formed by 6 subunits, two of which (TCRα and TCRβ) are responsible for recognising MHC linked to antigenic peptides, while the other four (CD3γ, CD3δ, CD3ε and CD3ζ) are responsible for the transmission of signals to the lymphocyte cytoplasm (reviewed in Alarcon, B., Gil, D., Delgado, P. and Schamel, W. W. (2003) *Immunol Rev,* 191, 38-46). One of the initial processes that occurs after binding of TCR by MHC is the activation of tyrosine kinases of the Src family, Lck and Fyn, which phosphorylase the tyrosines of the ITAM of the CD3 subunits, which in turn are converted into binding sites for the tyrosine kinases of the Syk family (ZAP70 and Syk). Until recently it was thought that this was the linear schema for signal transmission and that from the kinases of the Syk family (especially ZAP70) a diverging activation cascade occurred resulting in the activation of various transcription factors, including NFAT, the target of immunosuppressive drugs cyclosporine A and FK506 (Lin, J. and Weiss, A. (2001) *J Cell Sci,* 114, 243-244). Some years ago, the authors of the present invention discovered that on becoming activated, TCR undergoes a conformational change that results in the recruitment of the Nck adaptor directly to a proline-rich sequence (PRS) of the CD3ε subunit (Gil, D., Schamel, W. W., Montoya, M., Sanchez-Madrid, F. and Alarcon, B. (2002) *Cell,* 109, 901-912). This TCR-Nck interaction was shown to be essential for TCR activation by experiments involving the over-expression of the amino-terminal SH3.1 domain of Nck (which binds to CD3ε) and by the introduction of the APA1/1 antibody in T lymphocytes, which binds to PRS and blocks it.

DESCRIPTION OF THE INVENTION

An important problem with current immunosuppressive agents is their toxicity due, to the fact that they do not inhibit lymphocyte pathways specifically.

The present invention provides a more specific immunosuppressive compound for T lymphocytes and with fewer secondary effects than currently existing compounds, based on the blocking of TCR-Nck interaction.

Both the conformational change in TCR and the mechanism of initiation of signal transmission, a fundamental step for the recruitment of effector proteins, were taken into account in the section of the compound of the present invention.

The conformation change in TCR, which occurs after the binding of stimulatory antibodies and of MHC, was first demonstrated by a "pull down" assay, where TCR was inducibly bound to a matrix of the GST-Nck fusion protein. This biochemical assay does not enable individual identification of those cells where the TCR undergoes the conformational change. However, the authors of the present invention demonstrated that the APA1/1 antibody also recognises the conformational change (Risueno, R. M., Gil, D., Fernandez, E., Sanchez-Madrid, F. and Alarcon, B. (2005) *Blood,* 106, 601-608). The antibody can be used in preparations of T lymphocytes in culture and also in immunohistochemical sections. This reagent enables the demonstration of the existence of conformation change by a procedure other than "pull down" in addition to demonstrating that the conformational change occurs in vivo. Furthermore, the antibody recognises immune synapses formed between T lymphocytes and antigen presenting cells loaded with a peptide agonist, but not synapses formed by a partial agonist/antagonist. These data suggest that the conformational change in TCR could be behind the distinction between strong and weak agonists by T lymphocytes and could activate specific activation cascades during the recognition of strong ligands. This hypothesis seems to be corroborated by the fact that during development in the thymus, the conformational change (visualised by staining with APA1/1) occurs during recognition of ligands that induce negative selection but not during recognition of ligands that induce positive selection (Risueno, R. M., van Santen, H. M. and Alarcon, B. (2006) *Proc Natl Acad Sci USA.,* 103, 9625-9630). The only known consequence of conformational change in TCR is the exposure of the PRS on CD3ε, although the possibility that the conformational change is also transmitted to cytoplasmic regions of the other CD3 subunits and globally influences the whole process of initiation of signal transmission by TCR, including phosphorylation of the tyrosines of the ITAMs, cannot be discounted (Minguet, S., Swamy, M., Alarcon, B., Luescher, I. F. and Schamel, W. W. (2007) *Immunity.,* 26, 43-54). However, the recruitment of Nck to the PRS of CD3ε is a possible mechanism of the transmission of the conformation change to intracellular activation pathways (Gil, D., Schamel, W. W., Montoya, M., Sanchez-Madrid, F. and Alarcon, B. (2002) *Cell,* 109, 901-912).

In order to demonstrate the importance of Nck-CD3ε interaction in the activation of T lymphocytes and to validate this interaction as a target for immunomodulating agents, synthetic peptides were designed to mimic the sequence of PRS and which could block the Nck to CD3ε binding site. A peptide was obtained, denominated 11R085, that was 300 times more potent than the peptide with the native wild sequence in the inhibition of the interaction of CD3ε with the SH3.1 domain of Nck. Using this peptide, the proliferation of human T lymphocytes was specifically inhibited, both CD4+ and CD8+, in response to stimulation with anti-CD3 antibodies, with an I050 of approximately 20 μM, whereas the proliferation of human T lymphocytes dependent on a different receptor, IL2R, was practically unaffected by this peptide, even at 3-fold higher concentrations.

Therefore, peptide 11R085 inhibits the activation initiated by TCR but not the activation mediated by the other receptor, and so it is specific for the molecular target for which it was designed.

Peptide 11R085 also inhibits the production of IL2 and the proliferation induced by antigen in OT-I transgenic mouse primary lymphocytes with an I050 of approximately 5 μM. Thus, Nck-CD3ε interaction as a molecular target for immunosuppressor development has been validated.

Figure 1:
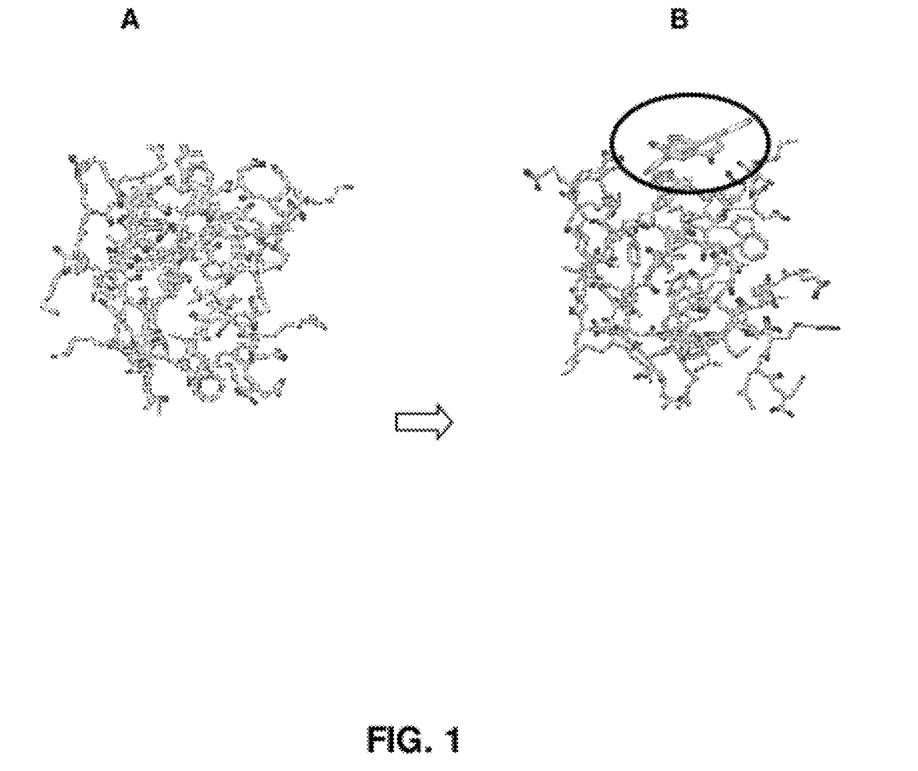
FIG. 1. Model of the SH3.1 domain and virtual screening of compounds with binding potential.

Using this information and bioinformatics selection strategies, virtual screening of compounds that bind to the SH3.1 domain was carried out as described in the examples of the invention. After this screening, the 10 candidates that best fitted into the SH3.1 hydrophobic pocket and could recognise the PRS sequence of CD3ε were selected (see FIG. 1). All these structurally very different compounds, had a certain degree of activity, but the one showing the highest activity and least toxicity, even at high doses (FIG. 7) was the compound denominated CBM-1, the compound with the structural formula (I).

Compound CBM-1 showed good activity and immunosuppressive capacity, inhibiting the proliferation of human T lymphocytes induced by anti-CD3 antibodies but not IL-2 dependent proliferation. It also inhibited the proliferation of antigen-dependent mouse T lymphocytes and the release of IL2. It inhibited the production of IFNγ, IL-10 and TNFβ, as well as the generation of human cells that produce IFNγ in response to anti-CD3 and anti-CD28 in human lymphocytes stimulated with anti-CD3 and anti-CD28 antibodies. These data verify that this compound has an inhibitory action on the activation of T lymphocytes, both in mice and humans, at concentrations as low as 0.1 μM, and preferably in the range between 0.1 and 1 μM.

Therefore, CBM-1 is active as an immunosuppressive agent.

Given the above, a first aspect of the present invention refers to a compound of formula (I):

(I)

or any of its derivatives, which include its salts, isomers or mixtures of isomers, prodrugs, crystalline forms, etc., for their use as pharmaceutical drugs, preferably as immunosuppressive agents.

Isomers or mixtures of isomers in the present invention are understood to mean:

1) Z or E isomers defined by the position of the substituents with respect to the multiple bonds of the compounds,
2) optical isomers or enantiomers, arising by the presence of chiral centres (atoms linked to four different substituents) resulting in differentiation between enantiomers with respect to their optical activity (rotation of polarised light after passing through a solution of the enantiomer),
3) diastereoisomers, isomers with at least two chiral centres, with the substituents of one of these centres being arranged equally in both diastereoisomers and the substituents of at least another of the centres being arranged differently in both.

The term "prodrugs" of compounds of formula (I) are understood to refer to any derivatives (e.g. esters, carbamates, amides, etc.) that when administered to an individual are able to provide, directly or indirectly, one or several of the compounds of this formula (I).

The definition of derivatives also includes "crystalline forms" of the compounds of formula (I) in a free state or as solvates. The term "solvate", as used here, includes both solvates that can be used in the composition of a drug and solvates useful in its preparation. Solvates can be obtained by conventional methods of solvation that are well known in the state of the art.

The term "salts" in the present invention are understood to be both pharmaceutically acceptable and unacceptable salts that can be useful in the preparation of drugs. Therefore all salts of the compounds of the invention, whether or not pharmaceutically acceptable, are included in the scope of the present invention.

Lastly, the definition of "derivatives" includes those compounds of the invention that contain one or more isotopically enriched atoms. For example, compounds with one of the formulae of the invention in which one or several hydrogen atoms have been replaced by deuterium or tritium atoms, one or several carbon atoms have been replaced by $^{13}C$ or $^{14}C$ atoms or one or several nitrogen atoms have been replaced by $^{15}N$.

The compound of formula (I) is able to bind to the SH3.1 domain of Nck, blocking TCR-Nck interaction, and therefore is a specific immunosuppressive agent of T lymphocytes that has clear advantages compared to other immunosuppressive agents, one of which is that it causes fewer secondary effects.

Therefore, an aspect of the invention is in the use of the compound with the structural formula (I) or any of its derivatives in the preparation of a drug for the treatment and/or prevention of diseases that are associated with the hyperproliferation of T lymphocytes.

These diseases are preferably autoimmune diseases, diseases associated with allotransplant or organ or tissue xenotransplant rejection, or lymphomas and/or T leukaemias.

The autoimmune diseases are more preferably those where the activation of T lymphocytes plays an important role in the induction and/or effector phase and more preferably the systemic organ-specific autoimmune diseases of the list comprising: multiple sclerosis and its varieties, systemic lupus erythematosus, psoriasis, vitiligo, rheumatoid arthritis, asthma, autoimmune hepatitis, type I diabetes, myasthenia gravis, ankylosing spondylitis, Crohn's disease, etc.

Another aspect of the invention is directed at a pharmaceutical composition comprising a compound of structural formula (I), or any of its previously described derivatives, and a pharmaceutically acceptable excipient.

In each case, the composition will adapt to the type of administration used. Therefore, the composition above can be presented in a pharmaceutical form for oral administration, either as a solid (e.g. tablets, pills, capsules, etc.) or liquid (e.g. solutions, suspensions, emulsions, etc.), for parenteral administration (e.g. intramuscular, subcutaneous, intravenous, etc.), rectal administration, etc., or any other form of clinically permissible administration and in a therapeutically effective amount.

The pharmaceutically acceptable adjuvants and vehicles that can be used in these compositions are the vehicles commonly used in the state of the art. The pharmaceutical composition provided by this invention can be given by any route of administration, so this composition will be formulated in a suitable pharmaceutical form for the selected administration route.

Throughout the description and the claims, the word "comprise" and its variants is not intended to exclude other technical characteristics, additives, components or steps. For experts in the field, other objects, advantages and characteristics of the invention will become apparent partly from the description and partly from the practice of the invention. The following figures and examples are provided by way of illustration only and are not intended to be limiting of the present invention.

DESCRIPTION OF THE FIGURES

Virtual screening of compounds that bind to the SH3.1 domain of Nck. Theoretical model of the structure of the SH3.1 domain of Nck (panel A). Panel B shows how one of these compounds fits into the upper part of the virtual model.

Proliferation was evaluated by flow cytometry in accordance with the loss of green fluorescence (CFSE) within the CD8+ population. The different compounds are represented by the NSI code followed by a number. CBM-1 is compound NSI-65.

Inhibition by CBM-1 of the proliferation of human T lymphocytes in response to stimulation with anti-CD3 antibodies. These results are compared with those of the proliferation of human IL2-dependent lymphoblasts.

Inhibition by CBM-1 of the secretion of cytokines by human T lymphocytes in response to stimulation with anti-CD3 antibodies. Peripheral blood mononuclear cells (PB-MNC) purified from healthy donors were stimulated on plates coated with anti-CD3 OKT3 antibodies in the presence of various doses of CBM-1 for 72 hours. The concentration of the indicated cytokines in the supernatant (IL-10, IFN-γ, and TFN-β) was evaluated by multiparametric flow cytometry (BD cytometric bead array). Compound CBM-1 did not show any effect on the release of IL5, IL1-β and IL6, whereas IL2 and IL4 were not detectable.

Intracellular expression of IFNγ in response to stimulation with a mixture of anti-CD3 and anti-CD28. The figure shows the expression of intracellular IFNγ (as the product of the percentage of positive cells and the average fluorescence) as a function of the concentration of CBM-1.

NMR structure of the SH3.1 domain of Nckα (A). The five β-sheets are numbered in consecutive order. N and C indicate the amino- and carboxy-terminal ends respectively. (B) Comparison of the residues displaced by binding of the 11R085 high affinity peptide to the SH3.1 domain of Nckα (in black) with the corresponding residues of Nckβ.

Displacements of the amino acid residues in the SH3.1 domain caused by the interaction with compound CBM-1. The lateral chains of the amino acids that changed their position after binding the compound are represented. The changes are consequent to the binding of compound CBM-1 to the pocket visualised in virtual screening.

Human Jurkat T lymphocyte cell line and human Raji lymphoblastoid B cell line were incubated with the indicated concentrations of CBM-1 for 48 hours. The toxicity of the compound was estimated by propidium iodide exclusion and flow cytometry. The two cell lines remained with 100% viability after 48 hours, even at the highest dose of the compound.

The positions of the β-sheets and connecting loops in the SH3.1 domain of Nckα are indicated. The black arrows indicate the residues that were strongly displaced after the binding of CBM-1.

EXAMPLES

The invention is illustrated below with some tests performed by the inventors that illustrate the work carried out to identify the compound of the invention and demonstrate its effectiveness.

Example 1

Effect of Peptides that Inhibit Nck-CD3ε Interaction on the Activation of T Lymphocytes In order to demonstrate the importance of Nck-CD3ε interaction in the activation of T lymphocytes and to validate this interaction as a target for immunomodulating agents, synthetic peptides were designed that mimic the sequence of PRS and could block the Nck to CD3ε binding site. A peptide was obtained, denominated 11R085, that was 300 times more potent than the peptide with the native wild sequence in the inhibition of the interaction of CD3ε with the SH3.1 domain of Nck. Using this peptide, the proliferation of human T lymphocytes was specifically inhibited, both CD4+ and CD8+, in response to stimulation with anti-CD3 antibodies with an IC50 of 20 μM, whereas the proliferation of human T lymphocytes dependent on a different receptor, IL2R, was practically unaffected by this peptide, even at 3-fold higher concentrations. This suggests that the peptide 11R085 inhibits the activation initiated by TCR but not the activation mediated by another receptor, and so it is specific for the molecular target for which it was designed. Peptide 11R085 also inhibited the production of IL2 and antigen-induced proliferation of OT-I transgenic mouse primary lymphocytes with an IC50 of 5 μM. Thus, Nck-CD3ε interaction as a molecular target for immunosuppressor development has been validated.

Example 2

Selection by Virtual Screening of Compounds with Potential to Block Nck-CD3ε Interaction and the Evaluation of their Immunosuppressor Capacity Molecular modelling techniques (Fiser, A., Feig, M., Brooks, C. L., 3rd and Sali, A. (2002) Acc. Chem. Res., 35, 413-421) were used to obtain the structure of the SH3.1 domain of Nckα by homology based on its sequence and on the structure of some 50 known SH3 domains of other proteins. In this way, a theoretical model of the structure was obtained that can be considered to be very similar to the real structure of the domain. Starting with this structure, virtual screening with our own software was performed on a collection of more than 300,000 compounds provided by the North American company Chembridge and ten compounds were selected that theoretically fit best into the hydrophobic pocket of SH3.1, which is believed to be responsible for recognition of the PRS sequence of CD3ε (see FIG. 1). These compounds were later used to perform assays of the inhibition of proliferation of human T lymphocytes stimulated with anti-CD3 antibodies.

Example 3

Selective Effect of the Compounds Resulting from the Virtual Screening on Proliferation Induced by Anti-CD3

For the next round of selection of the compounds resulting from virtual screening with potential for blocking Nck-CD3ε interaction, PBMNC purified from healthy donors were labelled with fluorescence and incubated for 5 days on plates covered with anti-CD3 OKT3 antibodies in the presence of different doses of these compounds. Proliferation of T lymphocytes was evaluated by flow cytometry in accordance with the loss of green fluorescence (CFSE) within the CD8+ population.

Figure 2:
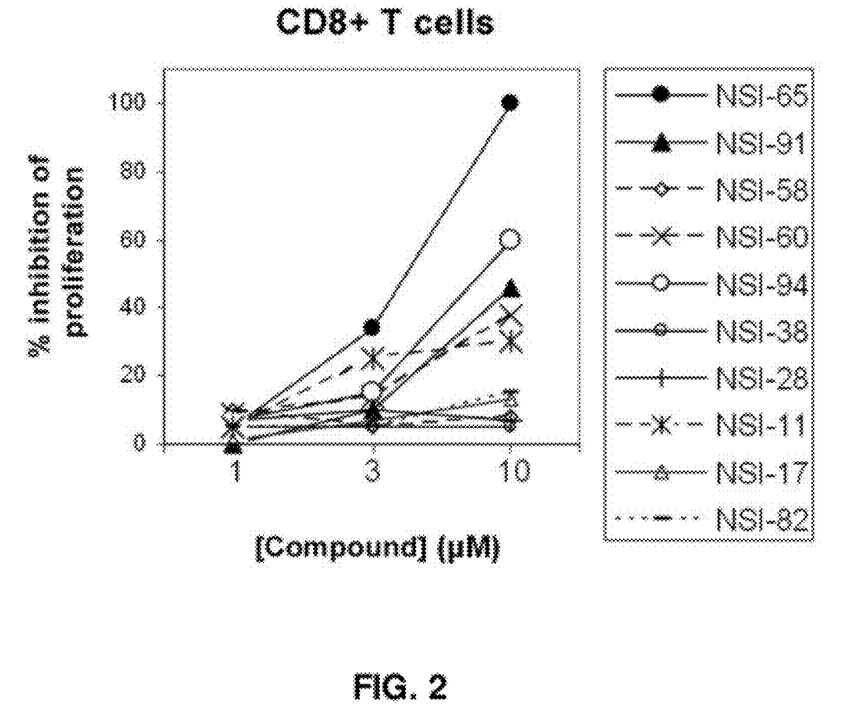
FIG. 2. Selective effect of the compounds resulting from the virtual screening on the proliferation induced by anti-CD3.

All the compounds tested had a certain degree of blocking activity on the proliferation of the lymphocytes, but the best and least toxic was the compound denominated CBM-1 (compound of the structural formula (I)), as shown in FIG. 2, where CBM-1 is represented by the compound NSI-65.

Example 4

Selective Effect of CBM-1 on the Proliferation Induced by Anti-CD3

PBMNCs purified from healthy donors were labelled with CFSE and incubated for 5 days on plates coated with anti-CD3 OKT3 antibody in the presence of various doses of the compounds indicated, among them CBM-1. The proliferation was evaluated by flow cytometry in accordance with the loss of green fluorescence (CFSE) within the CD4+ and CD8+ populations. A parallel experiment was performed on the proliferation of human IL2-dependent lymphoblasts. Purified PBMNC from healthy donors were stimulated with PHA for 48 hours and labelled with CFSE. The were subsequently cultured for 3 days in the presence of 100 IU/ml of human recombinant IL2 in the presence of concentrations of the compounds used, particularly CBM-1.

Figure 3:
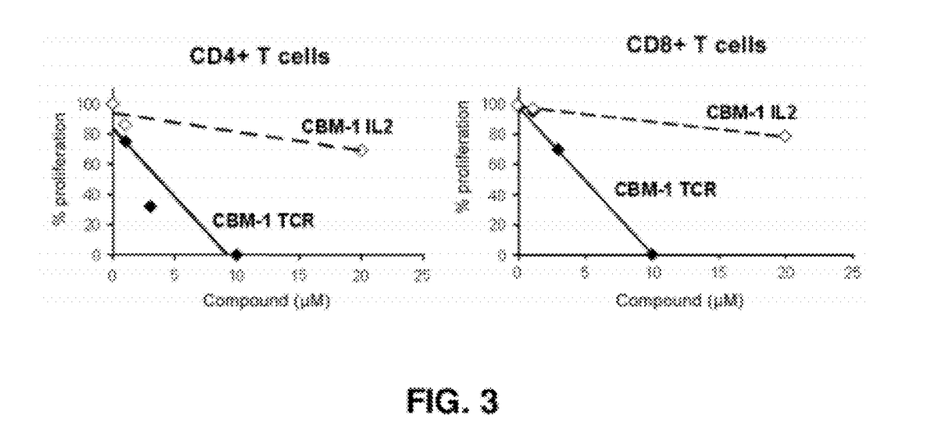
FIG. 3. Selective effect of compound CBM-1 on the proliferation induced by anti-CD3.

Compound CBM-1 inhibited the proliferation of CD4+ lymphocytes induced by anti-CD3 with an IC50 of 2 μM and that of CD8+ lymphocytes with an IC50 of 3 μM (FIG. 3). The inhibitory effect of the other compounds was slightly less. However, CBM-1 did not significantly inhibit the proliferation of human IL2-dependent lymphoblasts at concentrations of 20 μM, indicating its specificity for proliferation dependent on TCR activation but not that dependent on IL2R. This data supports a selective mechanism of action on TCR.

Example 5

Figure 4:
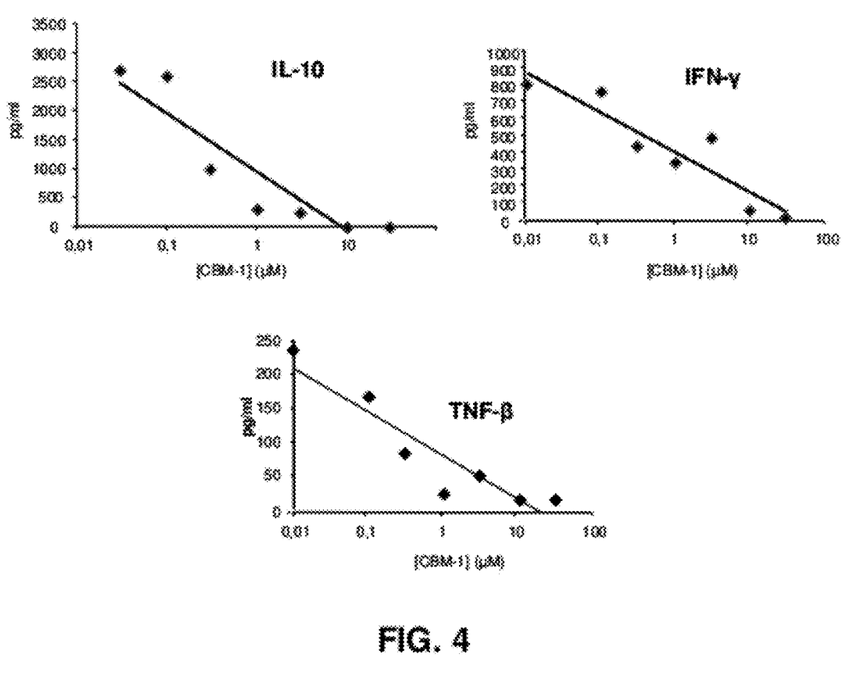
FIG. 4. Inhibition of the release of cytokines by CBM-1.

Inhibition of Cytokine Secretion by Human T Lymphocytes in Response to Stimulation with Anti-CD3 Antibodies The effect of CBM-1 on the production of cytokines was measured in an assay in which human PBMNC were stimulated with anti-CD3 antibodies. The supernatant of these cells was collected at 72 hours and several cytokines were simultaneously measured by a flow cytometry assay. These experiments demonstrated that the compound had a potent inhibitory effect on cytokines Th1 and IFNγ (1050 of 0.3 μM), TNFβ (1050 of 0.2 μM) and IL10 (1050 of 0.2 μM) and had no effect on the production of IL5 and IL6 up to concentrations of 30 μM (FIG. 4). The data indicated therefore that CBM-1 selectively inhibits the production of some cytokines by T lymphocytes, but not of others. That is to say, CBM-1 shows a degree of selectivity in the inhibition of intracellular signal transmission pathways.

Example 6

Figure 5:
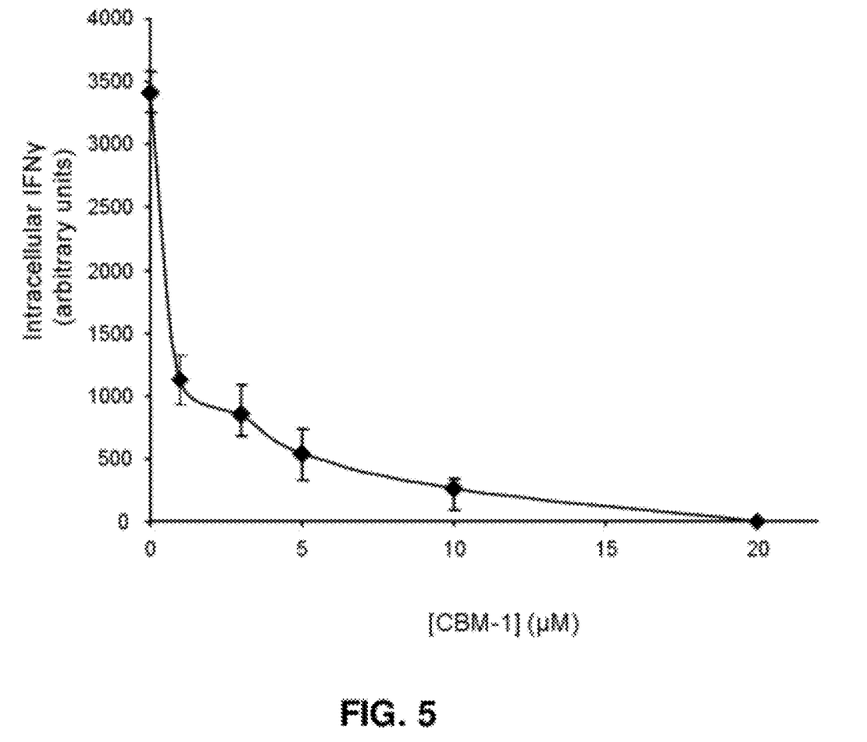
FIG. 5. Inhibition of intracellular production of IFNγ.

Inhibition of Intracellular IFNγ Expression by Mouse CD4+ T Cells in Response to Stimulation with Anti-CD3 Antibodies To demonstrate if inhibitors can prevent differentiation of Th0 into Th1 lymphocytes, differentiation assays were performed in vitro. C57BL/6 mouse spleen cells were stimulated with anti-CD3+ anti-CD28 antibodies for 48 hours in the presence of the indicated concentrations of CBM-1 and were incubated for a further 6 hours with brefeldin A. It was found that CBM-1 inhibited the generation of IFNγ-secreting Th1 lymphocytes with an 1050 of 0.8 μM. The cells were first stained with CD4-PE and after fixing and rinsing they were stained with anti-IFNγ antibody. The figure (FIG. 5) shows the expression of intracellular IFNγ (as the product of the percentage of positive cells and the average fluorescence) as a function of the concentration of CBM-1.

Example 7

NMR Determination of the Three-Dimensional Structure of the SH3.1 Domain of Nckα

Figure 6A:
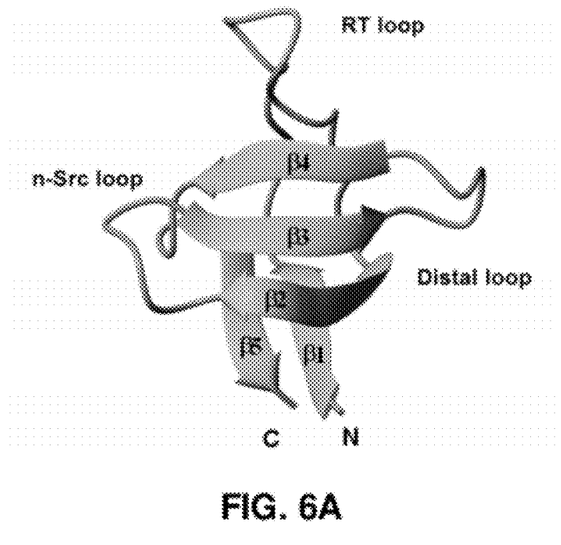
FIG. 6. NMR structure of the SH3.1 domain and displacements caused after the binding of the 11R085 high affinity peptide.
Figure 6B:
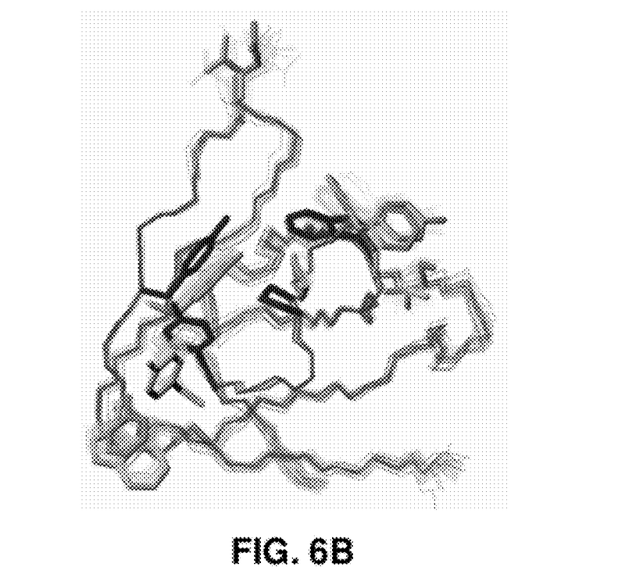
Figure 7:
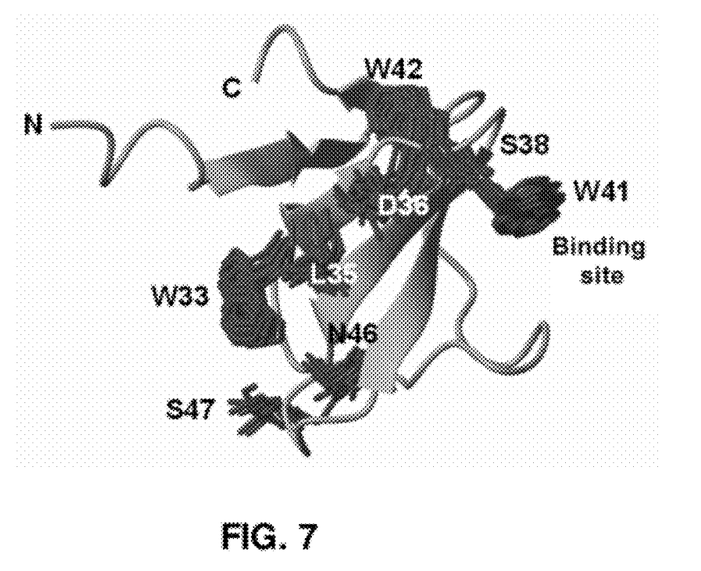
FIG. 7. NMR structure of the SH3.1 domain and displacements caused after the binding of CBM-1.
Figure 8:
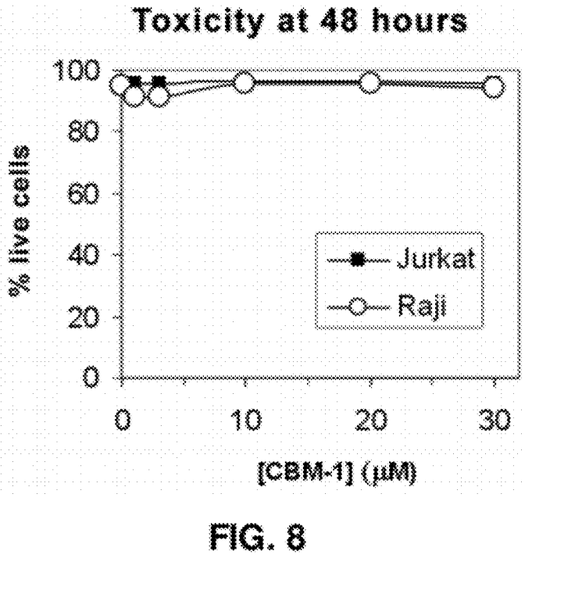
FIG. 8. Toxicity of CBM-1.

The three-dimensional structure of the SH3.1 domain of Nckα, in the presence and in the absence of peptide 11R085, was determined in parallel (with the collaboration of the laboratory of Professors María Angeles Jiménez and Manuel Rico, of the Instituto de Química-Física Rocasolano, CSIC, Madrid) (FIG. 6). This enabled validation of the prediction of the structural computer model used for virtual screening. In addition, it allowed measurement of the chemical displacements caused to the structure by compound CBM-1 (FIG. 7).

Figure 9:
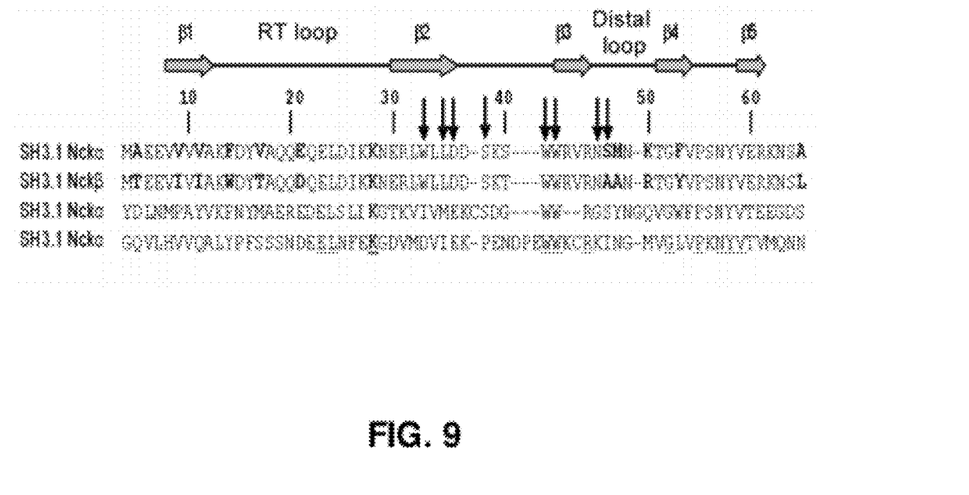
FIG. 9. Comparison of the primary sequence of the SH3.1 domain of Nckα with that of the SH3.1 domain of Nckβ and those of the SH3.2 and SH3.3 domains of Nckα.

The results indicated that CBM-1 interacts structurally with the protein approximately as predicted by the bioinformatics studies. The compound binds to a hydrophobic pocket with the participation of residues Trp41 and Tyr50/Phe53, causing a distortion and displacement of the β2-sheet and of residues in the distal loop (FIG. 7 and FIG. 9). The displacements of residues in the SH3.1 domain validate the prediction of the interaction of the SH3.1 domain with CBM-1 at a molecular level and are consistent with the model.

The invention claimed is:
1. Compound of formula (I):

for use as a medicinal drug.

2. A method for treatment of diseases that are associated with the activation of T lymphocytes or with their hyperproliferation or abnormal proliferation, the method comprising administering to a subject the compound of claim 1.

3. The method according to claim 2, where the diseases that are associated with the activation of T lymphocytes are autoimmune diseases.

4. The method according to claim 3, where the autoimmune diseases are selected from the group consisting of: multiple sclerosis, systemic lupus erythematosus, psoriasis, vitiligo, rheumatoid arthritis, asthma, autoimmune hepatitis, type I diabetes, myasthenia gravis, ankylosing spondylitis, and Crohn's disease.

5. The method according to claim 2 where the diseases that are associated with the activation of T lymphocytes are diseases associated with rejection of allotransplants or xenotransplants of organs or tissues.

6. The method according to claim 2, where the diseases that are associated with the activation of T lymphocytes are lymphomas or T-cell leukaemias.

7. A pharmaceutical composition comprising the compound according to claim 1 and a pharmaceutically acceptable excipient.

8. A method for inhibiting the activation of T lymphocytes comprising binding the compound of claim 1 to SH3.1 domain of Nck.

9. A method for inhibiting the activation of T lymphocytes comprising blocking TCR-Nck interaction with a compound of claim 1.

* * * * *